Figure 1:
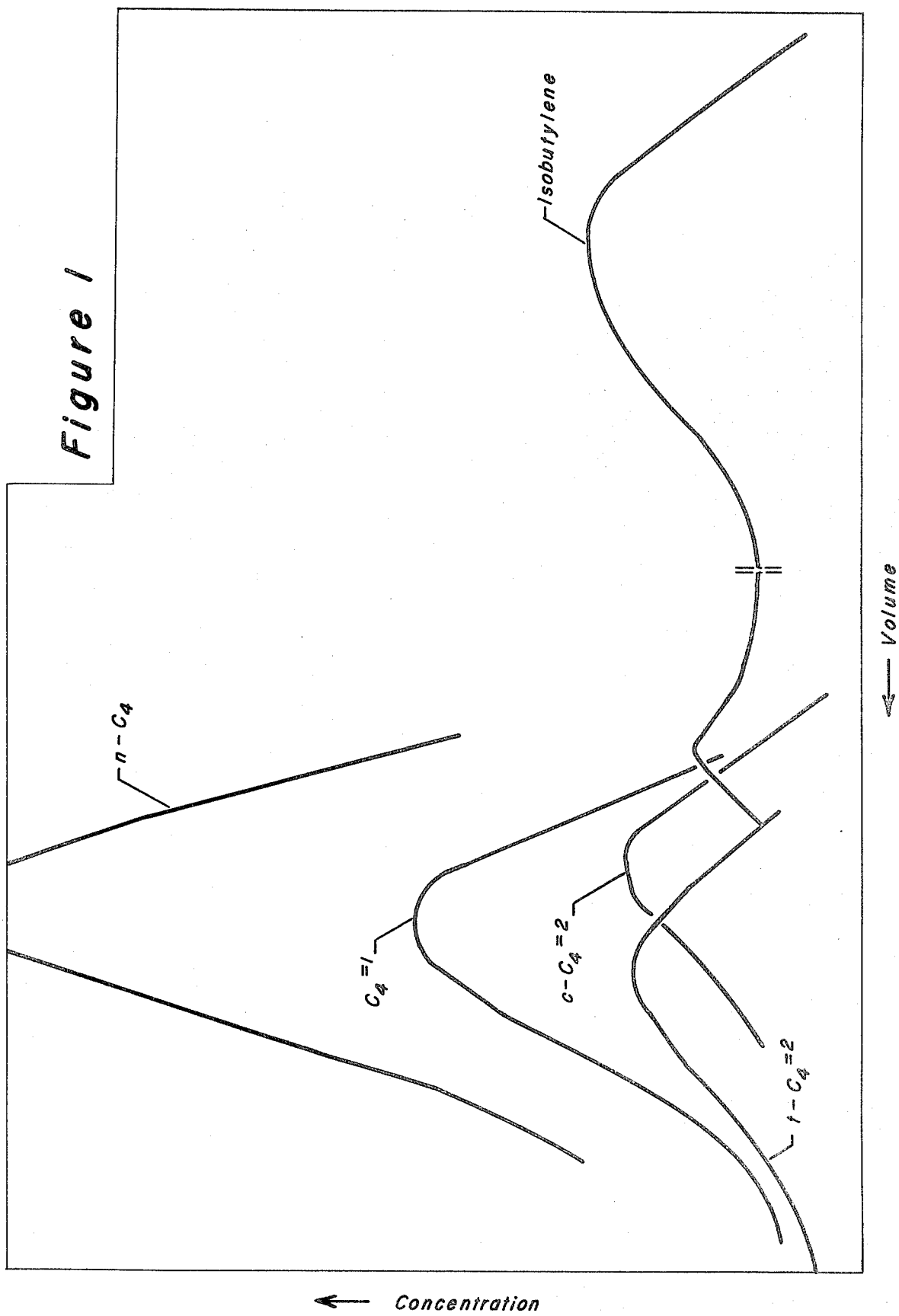

United States Patent [19]  [11]  4,455,445
Neuzil et al.  [45]  Jun. 19, 1984

[54] SEPARATION OF C₄ OLEFINS

[75] Inventors: Richard W. Neuzil, Downers Grove; Santi Kulprathipanja, Hoffman Estates, both of Ill.

[73] Assignee: UOP Inc., Des Plaines, Ill.

[21] Appl. No.: 451,525

[22] Filed: Dec. 20, 1982

Related U.S. Application Data

[63] Continuation-in-part of Ser. No. 357,371, Mar. 12, 1982, abandoned.

[51] Int. Cl.³ ............................................. C07C 7/13
[52] U.S. Cl. .................................. 585/820; 585/825; 585/826; 585/829; 208/310 Z
[58] Field of Search ............. 585/820, 825, 826, 829, 585/830; 252/455 Z, 449; 208/310 Z

[56] References Cited

U.S. PATENT DOCUMENTS

| | | | |
|---|---|---|---|
| 4,291,182 | 9/1981 | Dautzenberg et al. | 585/415 |
| 4,309,275 | 1/1982 | Mulaskey | 585/654 |
| 4,309,276 | 1/1982 | Miller | 585/654 |
| 4,309,281 | 1/1982 | Desseu | 585/820 |
| 4,320,241 | 3/1982 | Frankiewicz | 585/640 |
| 4,367,364 | 1/1983 | Kulprathipanja | 585/826 |

OTHER PUBLICATIONS

Wu et al., J. Phys. Chem., 82, 2777 (1979).
Anderson et al., J. Catalysis, 58, 114 (1979).
Olson et al., J. Catalysis, 61, 390 (1980).

Primary Examiner—Delbert E. Gantz
Assistant Examiner—A. Pal
Attorney, Agent, or Firm—James R. Hoatson, Jr.; Louis A. Morris; William H. Page, II

[57]  ABSTRACT

A process for the separation of normal C₄ hydrocarbons from isobutylene. A mixture of the normal C₄ hydrocarbons and isobutylene is contacted with a molecular sieve comprising silicalite which is selective for the normal C₄ hydrocarbons. The isobutylene is then recovered in the raffinate stream and the normal C₄ hydrocarbons recovered by displacement with pentene-1.

18 Claims, 2 Drawing Figures

SEPARATION OF C4 OLEFINS

CROSS REFERENCE TO RELATED APPLICATION

This application is a continuation-in-part of our prior copending application U.S. Ser. No. 357,371 filed Mar. 12, 1982 and now abandoned, incorporated herein by reference.

BACKGROUND OF THE INVENTION

It is highly desired to obtain an isobutylene rich product, since that butene is useful in gasoline blending and subsequent reactions to produce, e.g., butyl rubber and lubricating oil additive. Crystalline aluminosilicates are known in the art to be useful for separating hydrocarbons. Particularly some of the Type X or Type Y zeolites have been disclosed which relate to the separation of olefins from paraffinic hydrocarbons and the separation of butene-1 from isobutylene (see U.S. Pat. Nos. 3,723,561 to Priegnitz and 4,119,678 to Neuzil et al). Zeolites, however, have the propensity to cause dimerization or even polymerization of olefins and are thus not well suited for use as an adsorbent for the separation of present interest.

We have made the discovery that silicalite is able to effect the separation of normal $C_4$ hydrocarbons from isobutylene with substantially complete elimination of the aforementioned undesired side effects of dimerization and polymerization, particularly when pentene-1 is used to displace the normal $C_4$ hydrocarbons from the silicalite.

SUMMARY OF THE INVENTION

In one embodiment, the present invention is a process for separating isobutylene from a feed containing isobutylene and at least one normal $C_4$ hydrocarbon comprising contacting the feed at retention conditions with a molecular sieve comprising silicalite to effect selective retention of the normal $C_4$ hydrocarbon, removing the isobutylene from contact with the molecular sieve and recovering the normal $C_4$ hydrocarbon by displacement from the molecular sieve with a displacement fluid comprising pentene-1 at displacement conditions.

In another embodiment, the present invention comprises a process for separating isobutylene from a feed containing isobutylene and at least one normal $C_4$ hydrocarbon using a molecular sieve comprising silicalite, which process comprises the steps of: (a) maintaining net fluid flow through a column of the molecular sieve in a single direction, which column contains at least three separate and serially interconnected zones; (b) maintaining a retention zone defined by the feed inlet and raffinate outlet as a downstream boundary; (c) maintaining a purification zone defined by an extract outlet and the feed inlet as a downstream boundary; (d) maintaining a displacement zone defined by a displacement fluid inlet and said extract outlet as a downstream boundary; (e) passing the feed into the retention zone at retention conditions and retaining the normal $C_4$ hydrocarbon and withdrawing a raffinate stream containing isobutylene; (f) passing a displacement material comprising pentene-1 into the displacement zone at displacement conditions and displacing the normal $C_4$ hydrocarbon from the molecular sieve; (g) withdrawing an extract stream comprising the normal $C_4$ hydrocarbon and displacement fluid from the displacement zone; and, (h) periodically advancing through the column of molecular sieve in a downstream direction with respect to fluid flow the feed inlet, raffinate outlet, displacement fluid inlet, and extract outlet to shift zones through the molecular sieve.

Other embodiments of our invention encompass details about feed mixtures, molecular sieves, displacement materials and operating conditions, all of which are hereinafter disclosed in the following discussion of each of the facets of the present invention.

DESCRIPTION OF THE INVENTION

At the outset the definitions of various terms used throughout the specification will be useful in makino clear the operation, objects and advantages of our process.

A "feed mixture" is a mixture containing one or more extract components and one or more raffinate components to be separated by our process. The term "feed stream" indicates a stream of a feed mixture which passes to the molecular sieve used in the process.

An "extract component" is a compound or type of compound that is more selectively retained by the molecular sieve while a "raffinate component" is a compound or type of compound that is less selectively retained. In this process, a normal $C_4$ hydrocarbon is an extract component and isobutylene is a raffinate component. The term "displacement material or fluid" shall mean generally a material capable of displacing an extract component. The term "displacing stream" or "displacement fluid input stream" indicates the stream through which displacement material passes to the molecular sieve. The term "raffinate stream" or "raffinate output stream" means a stream through which a raffinate component is removed from the molecular sieve. The composition of the raffinate stream can vary from essentially 100% displacement material to essentially 100% raffinate components. The term "extract stream" or "extract output stream" shall mean a stream through which an extract material which has been displaced by a displacement material is removed from the molecular sieve. The composition of the extract stream, likewise, can vary from essentially 100% displacement material to essentially 100% extract components. At least a portion of the extract stream and preferably at least a portion of the raffinate stream from the separation process are passed to separation means, typically fractionators, where at least a portion of displacement material is separated to produce an extract product and a raffinate product. The terms "extract product" and "raffinate product" mean products produced by the process containing, respectively, an extract component and a raffinate component in higher concentrations than those found in the extract stream and the raffinate stream. Although it is possible by the process of this invention to produce a high purity isobutylene product at high recoveries, it will be appreciated that an extract component is never completely adsorbed by the adsorbent, nor is a raffinate component completely nonadsorbed by the adsorbent. Therefore, varying amounts of a raffinate component can appear in the extract stream and, likewise, varying amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of a normal $C_4$ hydrocarbon to that of less selectively retained isobutylene will be lowest in the raffinate stream, next highest in the feed mixture, and the highest in the extract stream. Likewise, the ratio of the concentration of less selectively retained isobutylene to that of a more selectively retained normal $C_4$ hydrocarbon will be highest in the raffinate stream, next highest in the feed mixture, and the lowest in the extract stream.

The term "selective pore volume" of the molecular sieve is defined as the volume of the molecular sieve which selectively retains an extract component from the feed mixture. The term "non-selective void volume" of the molecular sieve is the volume of the molecular sieve which does not selectively retain an extract component from the feed mixture. This volume includes the cavities of the molecular sieve which are capable of retaining raffinate components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve. When molecular sieve "passes" into an operational zone (hereinafter defined and described) employed in one embodiment of this process its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is a net entrainment of liquid into the zone by the molecular sieve. Since this net entrainment is a fluid present in the non-selective void volume of the molecular sieve, it in most instances comprises less selectively retained feed components.

Feed stocks which can be utilized in the process of this invention can be derived from any of the refinery processes known to the art. Specifically, the feed stocks include $C_4$ mono-olefinic hydrocarbons such as butene-1, isobutylene, trans-butene-2 and cis-butene-2. The term "butene-2" shall include both the cis- and transisomer configuration of that hydrocarbon. Other materials can be present in the feed stock such as large quantities of paraffinic or naphthene substances and in some instances low concentrations of aromatic hydrocarbons other than benzene and other contaminant substances such as the combined sulfur nitrogen compounds. It is preferred, however, to substantially reduce the quantity of components which would contribute to the deactivation of the molecular sieves by blocking off the selective pore passageways to feed stock components.

Specific feed stocks which can be utilized in the process of this invention include a feed stock containing about 35 vol.% butene-1, 32.5 vol.% isobutylene and 32.5 vol.% isobutane. Other feed stock compositions include feed stocks containing approximately 21 vol.% butene-1, 21 vol.% isobutylene, 16% trans-butene-2, 16% cis-butene-2 with remaining feed stock components comprising a butane component such as isobutane or normal butane. The feed stock can contain other paraffinic substances having higher molecular weight such as heptene or hexanes or octanes or nonanes or higher molecular weight paraffins. It is preferred to utilize feedstocks having more than about 15 vol.% total olefins.

Nonnormal hydrocarbons other than isobutylene, such as isobutane, will be rejected by the silicalite adsorbent and comprise part of the raffinate stream along with the isobutylene. This presents no problem if pure isobutylene is desired, since such hydrocarbons are easily separated from isobutylene by conventional means of distillation. The difficult separation is that of isobutylene from the normal hydrocarbons, particularly normal olefins, and that separation is accomplished by the present invention.

Desorbent materials or displacement fluids used in various prior art separation processes vary depending upon such factors as the type of operation employed. In the swing bed system in which the selectively retained feed component is removed from the molecular sieve by a purge stream displacement fluid, selection is not as critical and displacement materials comprising gaseous hydrocarbons such as methane, ethane, etc., or other types of gases such as nitrogen or hydrogen may purge the retained feed component from the molecular sieve. However, in molecular sieve separation processes which are generally operated continuously at substantially constant pressures and temperatures to insure liquid phase, the displacement material must be judiciously selected to satisfy many criteria. First, the displacement material should displace an extract component from the molecular sieve with reasonable mass flow rates without itself being so strongly retained as to unduly prevent an extract component from displacing the displacement material in a following retention cycle. Secondly, displacement materials must be compatible with the particular molecular sieve and the particular feed mixture. More specifically, they must not reduce or destroy the critical selectivity of the molecular sieve for an extract component with respect to a raffinate component. Displacement materials should additionally be substances which are easily separable from the feed mixture that is passed into the process. Both the raffinate stream and the extract stream are removed from the molecular sieve in admixture with displacement material and without a method of separating at least a portion of the displacement material, the purity of the extract product and the raffinate product would not be very high nor would the displacement material be available for reuse in the process. It is therefore contemplated that any displacement material used in this process will preferably have a substantially different average boiling point than that of the feed mixture to allow separation of at least a portion of displacement material from feed components in the extract and raffinate streams by simple fractional distillation, thereby permitting reuse of displacement material in the process. The term "substantially different" as used herein shall mean that the difference between the average boiling points between the displacement material and the feed mixture shall be at least about 5° C. The boiling range of the displacement material may be higher or lower than that of the feed mixture. Finally, displacement materials should also be materials which are readily available and therefore reasonable in cost. In the preferred isothermal, isobaric, liquid-phase operation of the process of our invention, we have found that displacement material comprising pentene-1 meet these requirements and is particularly effective. It is usually advantageous to mix the desorbent with a diluent not selectively retained by the molecular sieve such as isooctane or cyclohexane.

A dynamic testing apparatus is employed to test various molecular sieves with a particular feed mixture and displacement material to measure the molecular sieve characteristics of retention capacity and exchange rate. The apparatus consists of a molecular sieve chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the molecular sieve chamber. A pulse test, performed using this apparatus and the following general procedure. is used to determine selectivities and other data for various molecular sieve systems. The molecular sieve is filled to equilibrium with a particular displacement material by passing the displacement material through the molecular sieve chamber. At a convenient time, a pulse of feed containing known concentrations of a particular extract component or of a raffinate component or both, all diluted in displacement fluid, is injected for a duration of several minutes. Displacement fluid flow is resumed, and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, molecular sieve performance can be rated in terms of void volume, retention volume for an extract or a raffinate component, and the rate of displacement of an extract component by the displacement fluid. The retention volume of an extract or a raffinate component may be characterized by the distance between the center of the peak envelope of an extract or a raffinate component and the peak envelope of the tracer component or some other known reference point. It is expressed in terms of the volume in cubic centimeters of displacement fluid pumped during this time interval represented by the distance between the peak envelopes. The rate of exchange of an extract component with the displacement fluid can generally be characterized by the width of the peak envelopes at half intensity. The narrower the peak width, the faster the displacement rate. The displacement rate can also be characterized by the distance between the center of the tracer peak envelope and the disappearance of an extract component which has just been displaced. This distance is again the volume of displacement fluid pumped during this time interval.

The molecular sieve to be used in the process of this invention comprises the silicalite. As previously mentioned. silicalite is a hydrophobic crystalline silica molecular sieve. Due to its aluminum-free structure, silicalite does not show ion-exchange behavior, and is hydrophobic and organophilic. Silicalite thus comprises a molecular sieve, but not the hydrated aluminum or calcium silicate comprising a zeolite. Silicalite is uniquely suitable for the separation process of this invention for the presumed reason that its pores are of a size and shape that enable the silicalite to function as a molecular sieve, i.e. accept the molecules of normal $C_4$ hydrocarbons into its channels or internal structure, while rejecting the molecules of isobutylene. A detailed discussion of silicalite may be found in the article "Silicalite, A New Hydrophobic Crystalline Silica Molecular Sieve"; *Nature*, Vol. 271, Feb. 9, 1978, incorporated herein by reference.

The molecular sieve may be employed in the form of a dense compact fixed bed which is alternatively contacted with the feed mixture and displacement materials. In the simplest embodiment of the invention, the molecular sieve is employed in the form of a single static bed in which case the process is only semi-continuous. In another embodiment, a set of two or more static beds may be employed in fixed bed contacting with appropriate valving so that the feed mixture is passed through one or more molecular sieve beds, while the displacement materials can be passed through one or more of the other beds in the set. The flow of feed mixture and displacement materials may be either up or down throuoh the displacement fluid. Any of the conventional apparatus employed in static bed fluid-solid contacting may be used. The particles of silicalite molecular sieve will preferably have a particle size range of about 16–60 mesh (Standard U.S. Mesh).

Silicalite itself is a fine powder and therefore must be bound to obtain the above particle size. An inorganic oxide such as alumina is an acceptable binder, although a fluid permeable organic polymer is at least as effective, particularly polystyrenedivinylbenzene. The organic polymer offers the further advantage of greater resistance to dissolution of the molecular sieve.

Countercurrent moving bed or simulated moving bed countercurrent flow systems have a much greater separation efficiency than fixed molecular sieve bed systems and are therefore preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such a flow system are described in U.S. Pat. No. 2,985,589, incorporated herein by reference. In such as system, it is the progressive movement of multiple liquid access points down a molecular sieve chamber that simulates the upward movement of molecular sieve contained in the chamber. Only five of the access lines are active at any one time: the feed input stream, displacement fluid inlet stream, raffinate outlet stream, and extract outlet stream access lines. Coincident with this simulated upward movement of the solid molecular sieve is the movement of the liquid occupying the void volume of the packed bed of molecular sieve. So that countercurrent contact is maintained, a liquid flow down the molecular sieve chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the molecular sieve chamber into separate zones, each of which has a different function. In this embodiment of the process, it is generally necessary that three separate operational zones be present in order for the process to take place, although in some instances an optional fourth zone may be used.

The retention zone, zone 1, is defined as the molecular sieve located between the feed inlet stream and the raffinate outlet stream. In this zone, the feedstock contacts the molecular sieve, an extract component is retained, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the molecular sieve between the extract outlet stream and the feed inlet stream. The basic operations taking place in zone 2 are the displacement from the non-selective void volume of the molecular sieve by a circulating stream of any raffinate material carried into zone 2 by the shifting of molecular sieve into this zone and the displacement of any raffinate material retained within the selective pore volume of the molecular sieve or retained on the surfaces of the molecular sieve particles. Purification is achieved by passing a portion of extract stream material leaving zone 3 into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the displacement zone or zone 3. The displacement zone is defined as the molecular sieve between the displacement fluid inlet and the extract outlet stream. The function of the displacement zone is to allow a displacement material which passes into this zone to displace the extract component which was retained by the molecular sieve during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the molecular sieve between the raffinate outlet stream and the displacement fluid inlet stream. if used, is located immediately upstream with respect to the fluid flow to zone 3. Zone 4 would be utilized to conserve the amount of displacement fluid utilized in the displacement step since a portion of the raffinate stream which is removed from zone 1 can be passed into zone 4 to displace displacement material present in that zone out of that zone into the displacement zone. Zone 4 will contain enough molecular sieve so that raffinate material present in the raffinate stream passing out of zone 1 and into zone 4 can be prevented from passing into zone 3, thereby contaminating extract stream removed from zone 3. In the instances in which the fourth operational zone is not utilized, the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of molecular sieve can be accomplished by utilizing a manifold system in which the valves in the manifold are operated in a sequential manner to effect the shifting of the input and output streams, thereby allowing a flow of fluid with respect to solid molecular sieve in a countercurrent manner. Another mode of operation which can effect the countercurrent flow of solid molecular sieve with respect to fluid involves the use of a rotating disc valve in which the input and output streams are connected to the valve and the lines through which feed input, extract output, displacement fluid input and raffinate output streams pass are advanced in the same direction through the molecular sieve bed. Both the manifold arrangement and disc valve are known in the art. Specifically, rotary disc valves which can be utilized in this operation can be found in U.S. Pat. Nos. 3,040,777 and 3,422,848. Both of the aforementioned patents disclose a rotary-type connection valve in which the suitable advancement of the various input and output streams from fixed sources can be achieved without difficulty.

In many instances, one operational zone will contain a much larger quantity of molecular sieve than some other operational zone. For instance, in some operations the buffer zone can contain a minor amount of molecular sieve as compared to the molecular sieve required for the retention and purification zones. It can also be seen that in instances in which displacement fluid is used which can easily displace extract material from the molecular sieve, that a relatively small amount of molecular sieve will be needed in a displacement zone as compared to the molecular sieve needed in the buffer zone or retention zone or purification zone or all of them. Since it is not required that the molecular sieve be located in a single column, the use of multiple chambers or a series of columns is within the scope of the invention.

It is not necessary that all of the input or output streams be simultaneously used and, in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternatively and periodically shifted to effect continuous operation. In some instances, the connecting conduits can be connected to transfer taps which during the normal operations do not function as a conduit through which material passes into or out of the process.

It is contemplated that at least a portion of the raffinate output stream will pass into a separation means wherein at least a portion of the displacement fluid can be separated to produce a raffinate product containing a reduced concentration of displacement material. Preferably, but not necessary to the operation of the process, at least a portion of the extract output stream will also be passed to a separation means wherein an extract product containing a reduced concentration of displacement material may be obtained. The separation means will typically be a fractionation column, the design and operation of which is well known to the separation art.

Reference can be made to D. B. Broughton U.S. Pat. No. 2,985,589 and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Although both liquid and vapor phase operations can be used in many adsorptive or molecular sieve separation processes, liquid-phase operation is preferred for this process because of the lower temperature requirements and because of the higher yields of extract product that can be obtained with liquid-phase operation over those obtained with vapor-phase operation. Retention conditions will include a temperature range of from about 20° C. to about 200° C., with about 20° C. to about 100° C. being more preferred, and a pressure sufficient to maintain liquid-phase. Displacement conditions will include the same range of temperatures and pressures as used for retention conditions.

The size of the units which can utilize the process of this invention can vary anywhere from those of pilot-plant scale (see for example our assignee's U.S. Pat. No. 3,706,812) to those of commercial scale and can range in flow rates from as little as a few cc an hour up to many thousands of gallons per hour.

The following example is presented to illustrate the process of this invention. The example is not intended to unduly restrict the scope and spirit of the claims attached hereto.

EXAMPLE

In this example the above described pulse test apparatus was used to test the ability of inorganic oxide bound silicalite to separate isobutylene from a mixture of isobutylene, n-butane, cis- and transbutene-2 and butene-1. Two tests were run. In the first test the molecular sieve used was alumina bound silicalite, the displacement fluid was isooctane followed by a hexene-1 and isooctane mixture in the ratio of 60:40, respectively, the column temperature was 50° C. and the feed stream pulse was 10 ml of a mixture of the $C_4$ isomers in isooctane. In the second test the molecular sieve used was clay bound silicalite, the displacement fluid was a 50:50 mixture of pentene-1 and cyclohexane (in accordance with the present invention), the column temperature was 60° C. and the feed stream pulse was 10 ml of a mixture of the $C_4$ isomers in displacement fluid.

The reason why displacement in the first test was initiated with isooctane was to demonstrate at the onset that the separation was a molecular sieve action, i.e. all $C_4$ components of the feed other than the isobutylene were retained in the silicalite pores while the isobutylene remained in the void spaces from which it was easily flushed. The aspect of the tests of immediate interest was the relative ability of the hexene-1 or pentene-1 in Tests 1 and 2, respectively, to displace the retained $C_4$ components from the silicalite.

The column temperature difference in the two tests is not considered to have a significant effect on the results.

The results obtained from Tests 1 and 2 are presented in the following Table and attached FIGS. 1 and 2 which comprise the elution curves generated by pulse Tests 1 and 2, respectively.

TABLE

| Test | Retention Volume | | | | Half Width | | | |
|---|---|---|---|---|---|---|---|---|
| | $n\text{-}C_4$ | $C_4^{=1}$ | $T\text{-}C_4^{=2}$ | $C\text{-}C_4^{=2}$ | $n\text{-}C_4$ | $C_4^{=1}$ | $T\text{-}C_4^{=2}$ | $C\text{-}C_4^{=2}$ |
| 1 | 35.0 | 35.8 | 37.8 | 33.1 | 15.5 | 13.5 | 13.5 | 12.4 |
| 2 | 8.6 | 11.4 | 7.6 | 14.3 | 8.9 | 9.6 | 8.4 | 11.3 |

Figure 2:
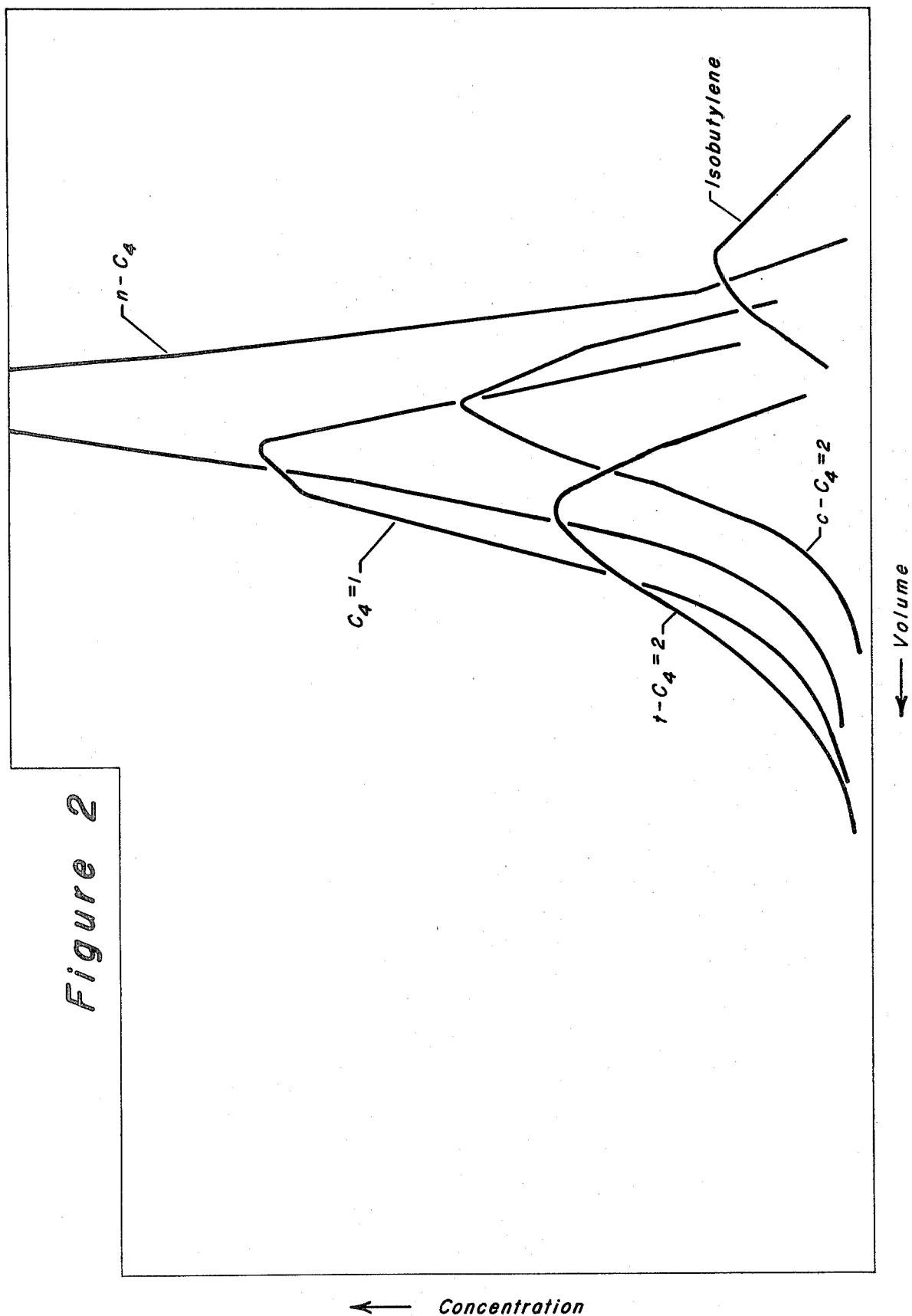

The isobutylene peak in FIG. 1 is shown separate and discontinuous from the other peaks because the isobutylene is eluted with the isooctane pre-flush and prior to the use of displacement fluid.

The data in the Table and the curves in the figures show the superior rate at which the pentene-1 effects displacement of the retained components (evident by lower retention volumes and half widths) as well as the fact of complete and "clean" displacement of such components achieved by pentene-1 as compared to the severe tailings experienced through use of the hexene-1. The effectiveness of the present invention is thus clearly illustrated.

The invention claimed is:

1. In a process for separating isobutylene from a feed containing isobutylene and at least one normal $C_4$ hydrocarbon comprising contacting said feed at retention conditions with a molecular sieve comprising silicalite to effect selective retention of said normal $C_4$ hydrocarbon, removing said isobutylene from contact with said molecular sieve, and recovering said normal $C_4$ hydrocarbon by displacement from said molecular sieve, the improvement which comprises performing said displacement with a displacement fluid consisting essentially of pentene-1 in solution with a diluent not selectively retained by said molecular sieve at displacement conditions.

2. The process of claim 1 wherein said retention conditions include a temperature within the range of from about 20° C. to about 200° C. and a pressure sufficient to maintain liquid phase.

3. The process of claim 1 wherein said displacement conditions include a temperature range within the range of from about 20° C. to about 200° C. and a pressure sufficient to maintain liquid phase.

4. The process of claim 1 wherein said displacement fluid contains from about 10 to about 90 LV% pentene-1.

5. The process of claim 1 wherein said diluent comprises isooctane or cyclohexane.

6. The process of claim 1 wherein said normal $C_4$ hydrocarbon comprises an olefin.

7. The process of claim 1 wherein said molecular sieve comprises silicalite bound with an inorganic oxide.

8. The process of claim 1 wherein said molecular sieve comprises silicalite bound with a fluid permeable organic polymer.

9. The process of claim 8 wherein said fluid permeable organic polymer comprises polystyrenedivinylbenzene.

10. A process for separating isobutylene from a feed containing isobutylene and at least one normal $C_4$ hydrocarbon using a molecular sieve comprising silicalite, which process comprises the steps of:
 (a) maintaining net fluid flow through a column of said molecular sieve in a single direction, which column contains at least three separate and serially interconected zones;
 (b) maintaining a retention zone defined by the feed inlet and raffinate outlet as a downstream boundary;
 (c) maintaining a purification zone defined by an extract outlet and said feed inlet as a downstream boundary;
 (d) maintaining a displacement zone defined by a displacement fluid inlet and said extract outlet as a downstream boundary;
 (e) passing said feed into said retention zone at retention conditions and retaining said normal $C_4$ hydrocarbon and withdrawing a raffinate stream containing isobutylene;

(f) passing a displacement material consisting essentially of pentene-1 in solution with a diluent not selectively retained by said molecular sieve into said displacement zone at displacement conditions and displacing said normal $C_4$ hydrocarbon from said molecular sieve;

(g) withdrawing an extract stream comprising said normal $C_4$ hydrocarbon and displacement fluid consisting essentially of pentene-1 in solution with a diluent not selectively retained by said molecular sieve from said displacement zone; and, (h) periodically advancing through said column of molecular sieve in a downstream direction with respect to fluid flow said feed inlet, raffinate outlet, displacement fluid inlet, and extract outlet to shift zones through said molecular sieve.

11. The process of claim 10 wherein said raffinate stream is passed to a separation means wherein said displacement fluid consists essentially of pentene-1 in solution with a diluent not selectively retained by said molecular sieve is removed from said stream to produce substantially pure isobutylene product.

12. The process of claim 11 wherein a buffer zone is maintained immediately upstream from said displacement zone, said buffer zone defined as the molecular sieve located between the displacement fluid inlet in a downstream boundary of said buffer zone and a raffinate outlet at an upstream boundary of said buffer zone.

13. The process of claim 10 wherein said retention and displacement conditions include a temperature within the range of from about 20° C. to about 200° C. and a pressure sufficient to maintain liquid phase.

14. The process of claim 10 wherein said displacement fluid contains from about 10 to about 90 LV% pentene-1.

15. The process of claim 10 wherein said diluent comprises iso-octane or cyclohexane.

16. The process of claim 10 wherein said molecular sieve comprises silicalite bound with inorganic oxide.

17. The process of claim 10 wherein said molecular sieve comprises silicalite bound with a fluid permeable organic polymer.

18. The process of claim 17 wherein said fluid permeable organic polymer comprises polystyrenedivinylbenzene.

* * * * *